United States Patent
Heimbecher et al.

(10) Patent No.: US 6,790,837 B2
(45) Date of Patent: Sep. 14, 2004

(54) RIBAVIRIN SYRUP FORMULATIONS

(75) Inventors: Susan K. Heimbecher, Morris Plains, NJ (US); Joel A. Sequeira, Edison, NJ (US)

(73) Assignee: Schering Corporation, Kenilworth, NJ (US)

( * ) Notice: Subject to any disclaimer, the term of this patent is extended or adjusted under 35 U.S.C. 154(b) by 156 days.

(21) Appl. No.: 10/285,119

(22) Filed: Oct. 31, 2002

(65) Prior Publication Data

US 2003/0087844 A1 May 8, 2003

Related U.S. Application Data

(60) Provisional application No. 60/334,751, filed on Oct. 31, 2001.

(51) Int. Cl.$^7$ ............................ A01N 43/04; A61K 31/70
(52) U.S. Cl. ................. 514/43; 514/2; 514/23; 514/27; 514/46; 536/28.6; 536/28.7; 536/29.1
(58) Field of Search ................. 514/43, 2, 23, 514/27, 46; 536/28.6, 28.7, 29.1

(56) References Cited

U.S. PATENT DOCUMENTS

| 4,211,771 | A | | 7/1980 | Witkowski .................. 424/180 |
| 4,880,784 | A | | 11/1989 | Robins et al. |
| 4,968,606 | A | * | 11/1990 | Yokozeki et al. ............. 435/42 |
| 5,767,097 | A | * | 6/1998 | Tam ............................ 514/43 |
| 6,423,695 | B1 | * | 7/2002 | Tam et al. .................... 514/81 |

FOREIGN PATENT DOCUMENTS

WO      WO99/62516      12/1999

OTHER PUBLICATIONS

PCT International Search Report, PCT/US02/34898 dated Jan. 31, 2003.
Patent Abstracts of Japan, Vo. 008, No. 034 (C–210) 58198416 A, Nov. 18, 1983.
Rebetol Package Insert, 2001.

* cited by examiner

*Primary Examiner*—Samuel Barts
*Assistant Examiner*—Patrick Lewis
(74) *Attorney, Agent, or Firm*—Robert J. Lipka

(57) ABSTRACT

A liquid formulation comprising ribavirin having a longer shelf life and improved taste is disclosed.

38 Claims, No Drawings

RIBAVIRIN SYRUP FORMULATIONS

This application claims benefit of priority to U.S. Provisional Patent Application 60/334,751, filed Oct. 31, 2001.

The present invention pertains to the field of liquid pharmaceutical formulations, and more particularly to syrup formulations containing ribavirin that have improved taste and stability.

Ribavirin is known to be useful in the treatment of hepatitis C as well as various other disease states. Ribavirin, 1β-D ribofuranosyl-1H-1,2,4 triazole 3-carboxamide, also known as Rebetol® in capsule form, or Virazole® in inhalable form, available from Schering Corporation, Kenilworth, N.J. and ICN Pharmaceuticals, Inc., Costa Mesa, Calif., respectively, is described in the Merck Index, compound No. 8199, Eleventh Edition. See also U.S. Pat. No. 4,211,771.

Certain patient populations exist that have difficulty in swallowing tablets or capsules. One common example of such a population is children. One solution to overcome the difficulty of administering certain medicaments is to provide the medicaments in a liquid formulation, e.g., in solution, emulsion, suspension or extract form. These liquid formulations are advantageous because they are easy to administer, and typically have organoleptic properties that make the formulation more palatable to the patient.

Syrup formulations are commonly used for delivery of pharmacological agents. Traditional syrups are concentrated solutions of sugar (generally sucrose) in purified water, such as Syrup, NF prepared with 850 grams sucrose and sufficient water to make 1000 mL according to the procedure given in the official monograph at page 1990 of NF XVII The National Formulary, United States Pharmacopeial Convention, Inc., Rockville, Md. U.S.A., 1990. As is well appreciated in the art, syrups frequently are flavored, such as with fruit or mint flavors, usually for purposes of masking an unpleasant taste caused by the presence of a dissolved or suspended pharmacologically active substance. A pleasant taste is particularly important when the formulation is intended for ingestion by children.

Due to the typically high sugar content in syrups, syrups are susceptible to microbial infestation. Syrups frequently must contain antimicrobial components to ensure safe storage without the proliferation of pathogenic molds, yeasts, bacteria and the like; a typical antimicrobial deemed suitable for use in foods and other ingestable substances is sodium benzoate.

A prime concern with any liquid formulation is the stability of the active ingredient, both short term and over time. In general, drug substances are less stable in aqueous media than in the solid dosage form. Thus, it is important to properly stabilize and preserve those formulations, especially if the formulation contains water. Chemical reactions can take place in these products that may involve ingredient-ingredient interaction. Another potential reaction is a container-product interaction that may alter pH, and thus, if the active ingredient is pH sensitive, instability in the form of precipitates or degradation products could result. Ribavirin is one such active ingredient that is pH sensitive, and it is readily degraded by hydrolysis when in a liquid formulation.

Prior art syrup formulations have been marketed by ICN that contain ribavirin as an active ingredient. These formulations, however, have certain disadvantages with regards to long term stability as compared to the syrups of the present invention. Ribavirin is readily degraded by hydrolysis in these formulations. Moreover, a solution pH that promotes hydrolysis will, in turn, affect ribavirin degradation directly by increasing the amount of ribavirin hydrolysis. Additionally, ribavirin stability is compromised when there is an increase in the formation of reducing agents in the formulation, i.e., the sugar sucrose can be hydrolyzed to the reducing sugars fructose and glucose. These sugars can in turn increase the hydrolysis of ribavirin. Accordingly, it is desired to provide a storage-stable liquid formulation of ribavirin that has an improved stability over time and is safe for ingestion by patients.

SUMMARY OF THE INVENTION

The present invention provides a liquid formulation comprising ribavirin, a buffering system, wherein the pH of the liquid formulation is in the range of about 4.8 to about 5.3, at least one pharmaceutically acceptable sweetening agent, and at least one pharmaceutically acceptable viscosity increasing agent.

The present invention also provides a pharmaceutically acceptable syrup formulation comprising ribavirin, a buffering system, wherein the pH of the pharmaceutically acceptable syrup formulation is in the range of about 4.8 to about 5.3, at least one pharmaceutically acceptable sweetening agent, and at least pharmaceutically acceptable one viscosity increasing agent.

The present invention also provides a pharmaceutically acceptable syrup formulation comprising ribavirin, a buffering system, said buffering system comprising sodium citrate dihydrate and citric acid anhydrous, wherein the pH of the pharmaceutically acceptable syrup formulation is in the range of about 4.8 to about 5.3, at least one pharmaceutically acceptable sweetening agent, and at least pharmaceutically acceptable one viscosity increasing agent.

DETAILED DESCRIPTION OF THE INVENTION

As used herein, the term concentration means the amount of an ingredient in grams per liter of the syrup, unless it is otherwise indicated.

As indicated above, the active ingredient of the present invention is ribavirin, available from Schering Corporation, Kenilworth, N.J. Ribavirin may be present in the formulation of this invention at a concentration of about 10 to about 60 grams/liter, more preferably, about 30 to about 50 grams/liter, and most preferably about 40 grams/liter.

As will be appreciated by one of ordinary skill in the art, the liquid formulations of the present invention may be a water based syrup formulations is having a high sugar content that increases the palatability of the formulation to the patient. Typically, as with most syrups, the formulation contains purified water in combination with sucrose. However, other sugars or sweeteners may be also used such as dextrose, sorbitol and glycerin, etc, for either taste masking or viscosity purposes. Pharmaceutically acceptable non-glycogenetic substances such as methylcellulose or hydroxyethylcellulose may be added to the formulation of the present invention to increase the viscosity, as well as artificial sweeteners for use in diabetic patients in need of treatment.

When sucrose is present, the concentration of sucrose is about 200 to about 500 grams/liter, preferably about 250 to about 350 grams/liter, most preferably about 300 grams/liter. A potential problem with sucrose, however, is the ready formation of dental caries. Accordingly, sugar substitutes may also be used. When sugar is used, it may be irradiated prior to formulating to prevent microbial growth. When sorbitol is present, the concentration of sorbitol can be about 50 to about 300 grams/liter, preferably about 100 to about 200 grams/liter, most preferably about 100 to about 140 grams/liter. When glycerol anhydrous USP is present, the concentration of glycerol anhydrous can be about 50 to about 300 grams/liter, preferably about 100 to about 200 grams/liter, and most preferably about 150 grams/liter.

Suitable buffer systems of use in the present invention include, by way of example only, tartaric, fumaric, maleic, phosphoric, and acetic acids and salts. Preferred buffering systems include citric acid and phosphoric acid buffer systems. The citric acid buffer system preferably contains sodium citrate dihydrate USP in combination with citric acid anhydrous USP, available from Haarman & Reimer. Preferably there is about 5.1 to about 5.4 grams/liter of sodium citrate dihydrate, most preferably 5.27 grams/liter of sodium citrate dihydrate, and about 2.05 to about 2.25 grams/liter of citric acid anhydrous, preferably about 2.15 grams/liter of citric acid anhydrous.

While the syrup of the present invention is a water based formulation, it is preferable to increase the non-aqueous proportion of the formulation because it is believed that a decrease in the non-aqueous portion of the formulation will increase the non-polar character of the formulation, thus decreasing ribavirin susceptibility to hydrolysis. Accordingly, in one aspect of the invention there can be present about 0 to about 200 grams/liter of propylene glycol, or preferably about 100 grams/liter.

The aqueous sugar medium is an efficient nutrient medium for growth of microorganisms. Hence, in certain formulations it is desirable to employ antimicrobial preservatives. The amount of a pharmaceutically acceptable preservative required to protect a syrup against microbial growth varies with the proportion of water available for growth, the nature and inherent preservative activity of some formulative materials (as many flavoring oils that are inherently sterile and possess antimicrobial activity), and the capability of the preservative itself. Among the preservatives commonly used in the preservation of syrups with the usually effective concentrations are benzoic acid (0.1 to 0.2%), sodium benzoate (0.1 to 0.2%), and various combinations of methyl-, propyl-, and butylparabens (totaling about 0.1%). Most preferred is sodium benzoate at a concentration of about 1 gram/liter.

Most syrups are flavored with synthetic flavorants or with naturally occurring materials such as volatile oils (e.g. orange oil), vanillin, and others, to render the syrup pleasant tasting. Because syrups are aqueous preparations, these flavorants must possess sufficient water-solubility. Typical flavoring agents which are commonly used in sweetened pharmaceuticals, foods, candies, beverages are also useful in the present invention; these materials may impart flavors such as grape, cherry, citrus, peach, strawberry, bubble gum, peppermint and many others are within the scope of the present invention. A preferred flavoring agent is Bubblegum Nat. and Art. #15864, available from Virginia Dare.

To enhance the appeal of the syrup, a pharmaceutically acceptable coloring agent is generally used which correlates with the flavorant employed (i.e. green with mint, brown with chocolate, etc.). The colorant used is generally water soluble, nonreactive with the other syrup components, and color-stable at the pH range and under the intensity of light that the syrup is likely to encounter during its shelf-life. The selection of an appropriate coloring agent is well within the skill of the art and is not added for safety purposes.

The syrup formulations of the present invention will be further illustrated by the following examples.

EXAMPLE 1

| Ingredients | Concentration g/L |
| --- | --- |
| Ribavirin | 40.0 |
| Sodium Citrate Dihydrate USP/EP | 5.27 |
| Citric Acid Anhydrous USP/EP | 2.15 |
| Sodium Benzoate NF/EP | 1.0 |
| Glycerol Anhydrous USP | 150.0 |
| Sucrose Extra Fine Granulated USP | 300.0 |
| Sorbitol Solution USP/EP | 142.0 |
| Propylene Glycol USP/EP | 100.0 |
| Flavoring Agent | 1.0 |
| Purified Water USP/EP | qs 1L |

To prepare the formulation, 35% of the final batch volume of the purified water was charged and heated to or at 60–80° C. The sugar, sodium benzoate, sodium citrate and citric acid were added and mixed until they dissolved. The solution was cooled to 25–30° C. The sorbitol and glycerin were added, followed by a pre-mix that contains propylene glycol and a flavorant mixed together. Finally, the ribavirin was added and dissolved. The batch was brought to final volume by weight, and subsequently passed through a 1.2 micron filter. Thereafter, the pH and specific gravity were measured.

The stability of a syrup formulation of the present invention was compared to conventional liquid formulations that contain ribavirin that are marketed by ICN. Degradation of syrup formulations containing ribavirin is observed during storage stability testing, as is evidenced by declining concentrations of the active ingredient and a concomitant formation of degradates. The most frequent degradation product that has been identified is the carboxylic acid product of ribavirin. Based upon these tests, it is believed that the syrup formulations of the present invention have a shelf life of greater than two years.

A comparative study was performed in which one sample of the ICN formulation and one sample of the formulation of the present invention of Example 1 were heated at 50° C. for a period of one month. The samples were then assayed to measure both ribavirin and its primary degradation product, ribavirin triazole carboxylic acid. As shown in the table below, the rate of ribavirin carboxylic acid formulation was more than five times faster in the ICN product then in the syrup formulation of the present invention.

TABLE 1

| | Initial Carboxylic Acid Content | 1 Month After Continuous 50° C. Temperature Carboxylic Acid Content |
| --- | --- | --- |
| ICN | 0.11% | 1.27% |
| Schering | 0.08% | 0.17% |

This analysis was performed via HPLC methods that are known to one of skill in the art. Stability data was also performed on the formulation of the present invention at 18 months after formulation, and measured by HPLC techniques as known by one of skill in the art as set forth in Table 2 below.

Only results that exceed the limit of quantitation (LOQ) were included in the attached tables. The LOQ of each degradation product is 0.05%. Synthesis-related impurities of ribavirin, the α-anomer and 5'-acetylribavirin, were not degradation products and are not monitored in the drug product. Each degradation product result was rounded to one significant figure according to the rounding convention described in the USP. The results for total degradation products that were derived from the sum of individual degradation products that contain one more significant figure than those shown in the data tables and then rounded to one decimal place.

Ribavirin did not degrade significantly after storage at 25° C./60% Relative Humidity ("RH") or 30° C./60% RH for up to 12 months or even at the ICH accelerated condition of 40° C./75% RH for up to 6 months.

The major degradation product of ribavirin in the syrup of the present invention at the intermediate and accelerated conditions is ribose triazole carboxylic acid (RTCOOH). The formation of this degradation product was most significant in the samples stored at 40° C./75% RH for about 6 months. RTCOOH levels rose from 0.08% to 0.3% under this ICH accelerated condition. Total degradation increased from 0.08% to 0.3% due to RTCOOH, after storage at 25° C./60% RH for up to about 12 months. Total degradation levels remained unchanged after storage at about 4° C. for up to about 12 months. RTCOOH and total degradation levels increased from approximately 0.08% to a range of about 0.1% to 0.2% after storage for about 12 months at 30° C./60% RH.

TABLE 2

| Batch | Assay % | RTCOOH | Assay | RTCOOH |
|---|---|---|---|---|
| Sample 1 | 99.8 | 0.06 | 100.0 | 0.11 |
| Sample 2 | 99.8 | 0.06 | 100.3 | 0.11 |
| Sample 3 | 99.3 | 0.06 | 99.2 | 0.11 |
| Sample 4 | 99.5 | 0.06 | 99.4 | 0.11 |

This data was assayed at about 18 months at 25° C. and 60% Relative Humidity.
The acceptance limits were set forth as such:

| | |
|---|---|
| Triazole Carboxamide (TCONH$_2$) | ≦0.1% |
| Triazole Carboxylic Acid (TCOOH) | ≦0.1% |
| Ribose Triazole Carboxylic Acid (RTCOOH) | ≦0.3% |
| Each Unspecified Degradation Product | ≦0.1% |
| Total Unspecified Degradation Products | ≦0.2% |
| Total Degradation Products | ≦0.6% |

The data presented in Table 2 demonstrate that the formulations prepared in accordance with Example 1 of the present invention show an improved stability profile over time as is evidenced by the minimal increase in degradation products after extended storage at the ICH conditions.

Accordingly, the invention has been set forth, and it is not limited in any fashion solely by the examples as set forth herein.

We claim:

1. A liquid formulation comprising ribavirin, a buffering system, wherein the pH of the liquid formulation is in the range of about 4.8 to about 5.3, at least one pharmaceutically acceptable sweetening agent, and at least one pharmaceutically acceptable viscosity increasing agent.

2. The liquid formulation according to claim 1, wherein the buffering system comprises sodium citrate dihydrate and citric acid anhydrous.

3. The liquid formulation according to claim 2, wherein the sodium citrate dihydrate is present in a concentration of about 5 grams/liter and the citric acid anhydrous is present in a concentration of about 2 grams/liter.

4. The liquid formulation according to claim 1, wherein the ribavirin is present in a concentration of about 20 to about 65 grams/liter.

5. The liquid formulation according to claim 4, wherein the ribavirin is present in a concentration of about 40 grams/liter.

6. The liquid formulation according to claim 1, wherein there is at least two pharmaceutically acceptable sweetening agents.

7. The liquid formulation according to claim 6, wherein the at least two pharmaceutically acceptable sweetening agents that are present are granulated sucrose and sorbitol solution.

8. The liquid formulation according to claim 7, wherein the granulated sucrose is present in a concentration of about 300 grams/liter and the sorbitol solution is present in a concentration of about 100 grams/liter to about 150 grams/liter.

9. The liquid formulation according to claim 7, further comprising at least one additional pharmaceutically acceptable sweetening agent.

10. The liquid formulation according to claim 1, wherein the at least one pharmaceutically acceptable viscosity increasing agent is propylene glycol USP.

11. The liquid formulation according to claim 10, wherein the propylene glycol USP is present in a concentration of about 100 grams/liter.

12. The liquid formulation according to claim 1, further comprising an antimicrobial agent.

13. The liquid formulation according to claim 1, wherein the liquid formulation is storage stable for at least 18 months.

14. A pharmaceutically acceptable syrup formulation comprising ribavirin, a buffering system, wherein the pH of the pharmaceutically acceptable syrup formulation is in the range of about 4.8 to about 5.3, at least one pharmaceutically acceptable sweetening agent, and at least one pharmaceutically acceptable viscosity increasing agent.

15. The pharmaceutically acceptable syrup formulation according to claim 14, wherein the buffering system comprises sodium citrate dihydrate and citric acid anhydrous.

16. The pharmaceutically acceptable syrup formulation according to claim 15, wherein the sodium citrate dihydrate is present in a concentration of about 5 grams/liter and the citric acid anhydrous is present in a concentration of about 2 grams/liter.

17. The pharmaceutically acceptable syrup formulation according to claim 14, wherein the ribavirin is present in a concentration of about 20 to about 65 grams/liter.

18. The pharmaceutically acceptable syrup formulation according to claim 17, wherein the ribavirin is present in a concentration of about 40 grams/liter.

19. The pharmaceutically acceptable syrup formulation according to claim 14, wherein there is at least two pharmaceutically acceptable sweetening agents.

20. The pharmaceutically acceptable syrup formulation according to claim 19, wherein the at least two pharmaceutically acceptable sweetening agents that are present are granulated sucrose and sorbitol solution.

21. The pharmaceutically acceptable syrup formulation according to claim 20, wherein the granulated sucrose is present in a concentration of about 300 grams/liter and the sorbitol solution is present in a concentration of about 100 grams/liter to about 150 grams/liter.

22. The pharmaceutically acceptable syrup formulation according to claim 19, further comprising at least one additional pharmaceutically acceptable sweetening agent.

23. The pharmaceutically acceptable syrup formulation according to claim 14, wherein the at least one pharmaceutically acceptable viscosity increasing agent is propylene glycol USP.

24. The pharmaceutically acceptable syrup formulation according to claim 23, wherein the propylene glycol USP is present in a concentration of about 100 grams/liter.

25. The pharmaceutically acceptable syrup formulation according to claim 14, further comprising an antimicrobial agent.

26. The pharmaceutically acceptable syrup formulation according to claim 14, wherein the pharmaceutically acceptable syrup formulation is storage stable for at least 18 months.

27. A pharmaceutically acceptable syrup formulation comprising ribavirin, a buffering system, said buffering system comprising sodium citrate dihydrate and citric acid anhydrous, wherein the pH of the pharmaceutically acceptable syrup formulation is in the range of about 4.8 to about 5.3, at least one pharmaceutically acceptable sweetening agent, and at least one pharmaceutically acceptable viscosity increasing agent.

28. The pharmaceutically acceptable syrup formulation according to claim 27, wherein the sodium citrate dihydrate is present in a concentration of about 5 grams/liter and the citric acid anhydrous is present in a concentration of about 2 grams/liter.

29. The pharmaceutically acceptable syrup formulation according to claim 27, wherein the ribavirin is present in a concentration of about 20 to about 65 grams/liter.

30. The pharmaceutically acceptable syrup formulation according to claim 29, wherein the ribavirin is present in a concentration of about 40 grams/liter.

31. The pharmaceutically acceptable syrup formulation according to claim 27, wherein there is at least two pharmaceutically acceptable sweetening agents.

32. The pharmaceutically acceptable syrup formulation according to claim 31, wherein the at least two pharmaceutically acceptable sweetening agents that are present are granulated sucrose and sorbitol solution.

33. The pharmaceutically acceptable syrup formulation according to claim 32, wherein the granulated sucrose is present in a concentration of about 300 grams/liter and the sorbitol solution is present in a concentration of about 100 grams/liter to about 150 grams/liter.

34. The pharmaceutically acceptable syrup formulation according to claim 31, further comprising at least one additional pharmaceutically acceptable sweetening agent.

35. The pharmaceutically acceptable syrup formulation according to claim 27, wherein the at least one pharmaceutically acceptable viscosity increasing agent is propylene glycol USP.

36. The pharmaceutically acceptable syrup formulation according to claim 35, wherein the propylene glycol USP is present in a concentration of about 100 grams/liter.

37. The pharmaceutically acceptable syrup formulation according to claim 27, further comprising an antimicrobial agent.

38. The pharmaceutically acceptable syrup formulation according to claim 27, wherein the pharmaceutically acceptable syrup formulation is storage stable for at least 18 months.

\* \* \* \* \*

UNITED STATES PATENT AND TRADEMARK OFFICE
CERTIFICATE OF CORRECTION

| | | |
|---|---|---|
| PATENT NO. | : 6,790,837 B2 | |
| APPLICATION NO. | : 10/285119 | |
| DATED | : September 14, 2004 | |
| INVENTOR(S) | : Susan K. Heimbecher | |

It is certified that error appears in the above-identified patent and that said Letters Patent is hereby corrected as shown below:

••in Claim 2, column 5, line 64, please add the term --ingredients-- after the term "system" and replace the term "comprises" with the term --comprise--

••in Claim 3, column 5, line 67, please delete the term "the"

••in Claim 3, column 6, line 1, please delete the term "the"

••in Claim 15, column 6, line 40, please add the term --ingredients-- after the term "system"

••in Claim 15, column 6, lines 40-41, please replace the term "comprises" with the term --comprise--

••in Claim 16, column 6, line 43, please delete the term "the"

••in Claim 16, column 6, line 44, please delete the term "the"

••in Claim 27, column 7, line 16, please add the phrase --whose ingredients comprise-- after the term "system"

••in Claim 27, column 7, lines 16-17 please delete the term "said buffering system comprising"

••in Claim 28, column 7, line 24, please delete the term "the"

UNITED STATES PATENT AND TRADEMARK OFFICE
CERTIFICATE OF CORRECTION

PATENT NO. : 6,790,837 B2
APPLICATION NO. : 10/285119
DATED : September 14, 2004
INVENTOR(S) : Susan K. Heimbecher It is certified that error appears in the above-identified patent and that said Letters Patent is hereby corrected as shown below:

••in Claim 28, column 7, line 25, please delete the term "the"

Signed and Sealed this

Twenty-seventh Day of March, 2007

JON W. DUDAS
*Director of the United States Patent and Trademark Office*